United States Patent
Kobayashi et al.

[11] Patent Number: 6,008,891
[45] Date of Patent: Dec. 28, 1999

[54] AUTOMATIC FLAW REMOVING METHOD FOR LONG MATERIALS

[75] Inventors: Hiroto Kobayashi; Yoshitomo Tamura, both of Himeji; Koji Kawamura, Sagamihara; Minoru Nakakusu, Yao, all of Japan

[73] Assignee: Sanyo Special Steel Co., Ltd., Hyogo-ken, Japan

[21] Appl. No.: 08/969,550

[22] Filed: Nov. 13, 1997

[30] Foreign Application Priority Data

Nov. 14, 1996 [JP] Japan ................................. 8-302853

[51] Int. Cl.⁶ .................................................. G01N 21/01
[52] U.S. Cl. ......................................................... 356/237.1
[58] Field of Search ........................ 356/237.1; 73/865.8, 73/622, 623; 324/237, 240, 220, 221; 209/517, 518; 364/507; 346/33

[56] References Cited

U.S. PATENT DOCUMENTS

| | | | |
|---|---|---|---|
| 4,126,491 | 11/1978 | Karlsson | 148/9.5 |
| 4,495,587 | 1/1985 | Plante et al. | 364/507 |
| 4,633,620 | 1/1987 | Lorenzi et al. | 51/165 R |
| 5,656,786 | 8/1997 | Curtis, Jr. et al. | 73/865.8 |

FOREIGN PATENT DOCUMENTS

| | | |
|---|---|---|
| 0423753A1 | 4/1991 | European Pat. Off. . |
| 1056482 | 1/1967 | United Kingdom . |

*Primary Examiner*—Frank G. Font
*Assistant Examiner*—Michael P. Stafira
*Attorney, Agent, or Firm*—Birch, Stewart, Kolasch & Birch, LLP

[57] ABSTRACT

An automatic flaw removing method for long materials, comprises the steps of: inspecting long materials, such as round-bar steels and steel pipes, for surface flaws by a flaw inspecting apparatus of all section to divide the long materials into rejected materials having a flaw(s) and accepted materials having no flaw; storing information on the longitudinal position and length of each of the flaws of the rejected materials in a storage unit; sequentially carrying out the tracking of each of the rejected materials; moving a circumferential flaw probe directly connected to a grinder, to a longitudinal coordinate position of each of the flaws of the rejected materials, on the basis of the information on the longitudinal position of each of the flaws stored in the storage unit, when each of the rejected materials arrives at a flaw grinding position; rotating each of the rejected materials; identifying a circumferential position of each of the flaws by picking up a flaw indicative signal by the circumferential flaw probe; and automatically grinding each of the rejected materials, on the basis of the information on the identified circumferential position of each of the flaws and the information on the longitudinal position and length of each of the flaws stored in the storage unit. Thus, it is possible to interlock a high-speed automatic flaw inspecting apparatus with an automatic grinder to automatically remove surface flaws of long materials.

5 Claims, 1 Drawing Sheet

AUTOMATIC FLAW REMOVING METHOD FOR LONG MATERIALS

BACKGROUND OF THE INVENTION

1. Field of the Invention

The present invention relates generally to an automatic flaw removing method for long materials. More specifically, the invention relates to an automatic flaw removing method, which inspects long materials, such as round-bar steels and steel pipes, for surface flaws by means of a flaw detecting apparatus of all section to automatically grind the materials having a flaw(s) on the basis of the flaw-position information.

2. Description of the Prior Art

As an example of a conventional automatic flaw removing method for long materials, Japanese Patent Publication No. 52-15054 discloses "a flaw-position defining method in a separate automatic flaw removing apparatus". In this method, a flaw inspecting apparatus is arranged so as to be separated from a grinder. In addition, during inspection, a reference point, such as a label which can be detected by optical means, is provided on a material to be processed. During grinding, the reference point is compared with the positional information of a flaw(s) detected by an optical detector to control the grinding position of the grinder.

In such a conventional method, as described above, a label is attached to a material to be detected, such as a round-bar steel, or a quick drying ink or paint is sprayed thereon. Therefore, the conventional method is not sufficient to accurately define the positions of the flaws, various flaw-patterns and so forth. In particular, it is difficult to apply the conventional method to a line of a high flaw-detecting rate (e.g., above 100 m/min), a material of a small-diameter curve and so forth.

In addition, in a case where an ultrasonic flaw detector using water is located immediately downstream of a surface inspecting apparatus, the label may be removed or the marking may run, so that it is difficult to apply the conventional method to an automatic flaw removing apparatus, which is required to have the accuracy and certainty of the position of the origin.

Moreover, during flaw detection, the material may travel while being twisted due to friction on a carrier roll and so forth. When a single reference mark is used, the flaw-position information map may also be twisted to be inaccurate, so as to cause the dislocation of the automatic grinding.

SUMMARY OF THE INVENTION

It is therefore an object of the present invention to eliminate the aforementioned problems and to provide an automatic flaw removing method for long materials, which can automatically remove surface flaws of long materials by interlocking a high-speed automatic flaw inspecting apparatus with an automatic grinder.

In order to accomplish the aforementioned and other objects, according to one aspect of the present invention, an automatic flaw removing method for long materials, comprises the steps of: inspecting long materials, such as round-bar steels and steel pipes, for surface flaws by means of a flaw inspecting apparatus of all section to divide the long materials into rejected materials having a flaw(s) and accepted materials having no flaw; storing information on the longitudinal position and length of each of the flaws of the rejected materials, in a storage unit; sequentially carrying out the tracking of each of the rejected materials; moving a circumferential flaw probe directly connected to a grinder, to a longitudinal coordinate position of each of the flaws of the rejected materials, on the basis of the information on the longitudinal position of each of the flaws stored in the storage unit, when each of the rejected materials arrives at a flaw grinding position; rotating each of the rejected materials; identifying a circumferential position of each of the flaws by picking up a flaw indicative signal by means of the circumferential flaw probe; and automatically grinding each of the rejected materials, on the basis of the information on the identified circumferential position of each of the flaws and the information on the longitudinal position and length of each of the flaws stored in the storage unit.

According to the present invention, the flaw inspecting apparatus may be a leakage-flux flaw detector or an eddy current flaw detector. In addition, the flaw inspecting apparatus may be either in the form that a sensor rotates and a material goes straight on, or in the form that a sensor is fixed and a material rotates.

According to the present invention, the information on the longitudinal position of each of the flaws, which is obtained by the flaw inspecting apparatus, is tracked to a grinding table while being synchronized with the material. If the circumferentially divided informations on each of the flaws are also incorporated into the information on the longitudinal position of each of the flaws, the distribution of the numbers of the flaws can be previously recognized, so that the information on the distribution can be used as an information source for the effective control of the grinder.

According to the present invention, the circumferential flaw-position probe may be a probe having the same flaw detectability as those of usual flaw inspecting apparatuses of all section. In addition, since the automatic grinder is directly connected to the circumferential flaw-position probe, there is little mechanical dislocation between the probe and the grinder, so that it is possible to surely grind the sought flaws.

According to the present invention, the automation of the surface flaw removing operation can be achieved by incorporating a high-speed automatic surface flaw detecting apparatus with an automatic grinder although it could not carry out the conventional flaw finding and removing operations by the magnetic particle inspection, which need the skill of an operator. In addition, the sensory test and the manual flaw removing operation, which depend on the level of performance of the operator, can be mechanized, so that it is possible to reduce operation errors, such as oversight, to improve the quality of products.

BRIEF DESCRIPTION OF THE DRAWING

The present invention will be understood more fully from the detailed description given herebelow and from the accompanying drawing of the preferred embodiment of the invention. However, the drawing is not intended to imply limitation of the invention to a specific embodiment, but are for explanation and understanding only.

DESCRIPTION OF THE PREFERRED EMBODIMENT

Figure 1:
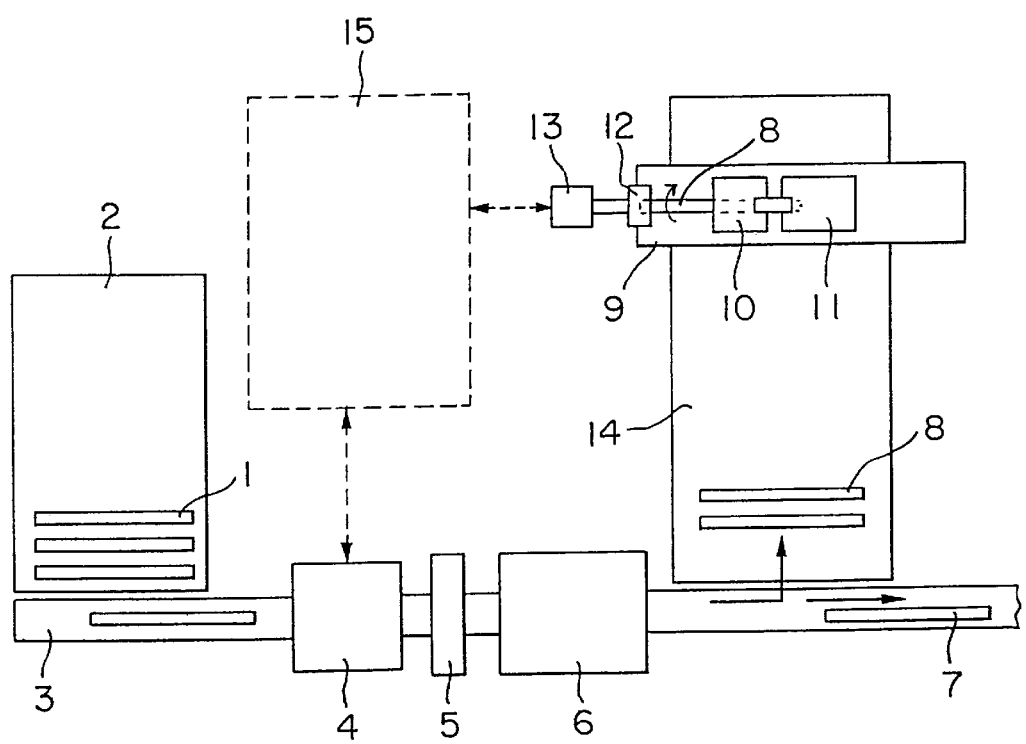
FIG. 1 is a schematic diagram of the preferred embodiment of an automatic flaw removing method according to the present invention.

Referring now to the accompanying drawing, the preferred embodiment of an automatic flaw removing method, according to the present invention, will be described below.

FIG. 1 is a schematic diagram of the preferred embodiment of an automatic flaw removing method according to the present invention.

In this preferred embodiment, round-bar steels ø20~ø80 were used. Materials 1 are kicked in an inspection table 3 from a delivering table 2. Then, the materials 1 are inspected for surface flaws by means of a rotary leakage-flux flaw detector 4. The position of each of flaws of rejected materials 8 having a flaw(s) (materials required to be trimmed) is marked every unit, which is circumferentially divided into 16 pieces, by means of a marking unit 5. Thereafter, each of the rejected materials 8 passing through a rotary ultrasonic flaw detector 6 is rejected to be put on a reject table 14.

The inspection rate of the inspection table 3 is relatively high, in the range of from 80 to 120 m/min. In addition, since the rotary ultrasonic flaw detector 6 using water as a contact medium is arranged on the reverse surface of the inspection table 3, the origin marking or labeling can not be achieved. Therefore, the marking by the marking unit 5 is carried out for confirmation.

The materials accepted by the rotary leakage-flux flaw detector 4 serve as accepted materials 7 having no flaw (materials not required to be trimmed) to go straight on without being rejected. That is, only the rejected materials 8 (the materials required to be trimmed) are arranged on the reject table 14. The accepted materials 7 (the materials not required to be trimmed) may pass through a grinding table 9. Although it is not always required to divide the long materials into non-defective materials and defective materials, the long materials are preferably divided in such a manner to improve the efficiency.

The information on each of the flaws of the rejected materials 8 (the materials required to be trimmed) is processed by means of a signal processing unit 15 of the rotary leakage-flux flaw detector 4 to be stored therein. When each of the rejected materials 8 (the materials required to be trimmed) arrives at the grinding table 9 by tracking, a control signal is transmitted to a control unit of a grinder 11.

That is, on the basis of flaw map information stored in the signal processing unit 15, a flaw probe 10 moves to the center of each of the flaws in longitudinal directions. Each of the rejected materials 8 is chucked by a chucking device 12, and rotated by a material rotating device 13 to seek and identify the circumferential position of each of the flaws. Then, each of the rejected materials 8 is fixed so as to turn the flaw toward right above. Thereafter, a grinding tool of the automatic grinder 11 directly connected to the flaw probe 10 moves downwards to one of the rejected materials 8 and removes the flaws while moving in longitudinal directions. If one of the rejected materials 8 has a plurality of flaws, each of the circumferential positions thereof is identified, and the flaw is turned toward right above, so that the grinding operations are repeated.

The main functions of the signal processing unit 15 are to collectively carry out the preparation and storage of a flaw map, the tracking of the flaw map, the position control of the flaw probe 10, the controls of the position and grinding conditions of the grinder 11.

Thus, the grinding is carried out while identifying the circumferential position of each of flaws, so that it is possible to surely remove the flaws under no influence of the bending of the material and the dislocation of the material due to chucking.

In addition, according to the conventional origin marking method, it is not possible to cope with the circumferential dislocation due to the twisted traveling of the material 1 when sampling flaw data by means of the rotary leakage-flux flaw detector 4. However, according to the method of the present invention, it is possible to identify the position of each of flaws to carry out the grinding thereof.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modification to the shown embodiment which can be embodied without departing from the principle of the invention as set forth in the appended claim.

What is claimed is:

1. An automatic flaw removing method for long materials each having a circular cross-section, said method comprising the steps of:

inspecting the long materials for surface flaws by means of a flaw inspecting apparatus so as to divide the long materials into rejected materials each having a flaw and accepted materials having no flaw, and so as to obtain information on a longitudinal position and a length of the flaw of each of the rejected materials;

storing the information on the longitudinal position and a length of the flaw of each of the rejected materials, in a storage unit;

sequentially carrying out the tracking of each of the rejected materials;

holding the rejected material by means of a chucking device, when each of the rejected materials arrives at a flaw grinding position;

moving a circumferential flaw probe directly connected to a grinder, to a longitudinal coordinate position of the flaw of the rejected material, on the basis of the information on the longitudinal position of the flaw stored in the storage unit;

identifying a circumferential position of the flaw by picking up a flaw indicative signal by means of said circumferential flaw probe, while rotating the rejected material held by the chucking device; and automatically grinding the rejected material held by the chucking device, on the basis of the information on the identified circumferential position of the flaw and the information on the longitudinal position and the length of the flaw stored in the storage unit, wherein each of the rejected materials is continuously held by the chucking device throughout the identifying step and the grinding step, after the holding step has been executed.

2. The method according to claim 1, wherein the step of automatically grinding includes the steps of:

rotating the rejected material so that the flaw faces to the grinder, on the basis of the information on the identified circumferential position of the flaw; and grinding the rejected material, while moving the grinder in a longitudinal direction of the rejected material, on the basis of the information on the longitudinal position and the length of the flaw stored in the storage unit.

3. The method according to claim 1, wherein the information on the longitudinal position of each of the flaws is tracked to a grinding table containing the grinder while being synchronized with the rejected materials.

4. The method according to claim 1, wherein the long materials are round bars.

5. The method according to claim 1, wherein the long materials are round pipes.

* * * * *